United States Patent
Trosper et al.

(10) Patent No.: US 10,588,656 B2
(45) Date of Patent: Mar. 17, 2020

(54) THROMBECTOMY CATHETER

(71) Applicant: Penumbra, Inc., Alameda, CA (US)

(72) Inventors: Nicole Trosper, Oakland, CA (US); Holly Sit, San Ramon, CA (US); Kathleen Lockhart, San Francisco, CA (US); Stephany Lai, San Francisco, CA (US)

(73) Assignee: Penumbra, Inc., Alameda, CA (US)

( * ) Notice: Subject to any disclaimer, the term of this patent is extended or adjusted under 35 U.S.C. 154(b) by 10 days.

(21) Appl. No.: 16/006,747

(22) Filed: Jun. 12, 2018

(65) Prior Publication Data

US 2019/0142452 A1  May 16, 2019

Related U.S. Application Data

(60) Provisional application No. 62/584,326, filed on Nov. 10, 2017.

(51) Int. Cl.
*A61B 17/3207* (2006.01)
*A61B 17/00* (2006.01)

(52) U.S. Cl.
CPC ........ *A61B 17/320758* (2013.01); *A61B 17/320783* (2013.01); *A61B 2017/00398* (2013.01); *A61B 2017/00778* (2013.01); *A61B 2217/005* (2013.01)

(58) Field of Classification Search
CPC ............ A61B 17/22; A61B 17/320758; A61B 2017/22075; A61B 2017/22079
See application file for complete search history.

(56) References Cited

U.S. PATENT DOCUMENTS

| 2,701,559 A | 2/1955 | Cooper |
| 3,082,805 A | 3/1963 | Royce |
| 3,614,953 A | 10/1971 | Edward |
| 3,683,891 A | 8/1972 | Eskridge et al. |

(Continued)

FOREIGN PATENT DOCUMENTS

| CN | 201341930 Y | 11/2009 |
| EP | 0533320 A2 | 3/1993 |

(Continued)

OTHER PUBLICATIONS

"International Search Report for PCT/US2018060086 dated Feb. 5, 2019 with Application as filed Nov. 9, 2018".

*Primary Examiner* — Julie A Szpira
(74) *Attorney, Agent, or Firm* — Wilson Sonsini Goodrich & Rosati

(57) ABSTRACT

A target substance, such as a thrombus, is removed from a patient's body via minimally invasive technique. A catheter is maneuvered and positioned near the target substance. The catheter may have a soft, atraumatic tip constructed from a metallic backbone covered by a polymer. Target substances are drawn into the catheter via an aspiration source. Near the catheter's distal end, a blade and opposing surface are housed within the catheter, and the blade moves relative to the opposing surface within the catheter lumen in order to fragment the target substance. The substances are fragmented within the catheter into discreet and relatively uniform particles. The aspiration source, which helps ensnare target substances, also serves to evacuate the substance fragments from the patient's body.

30 Claims, 5 Drawing Sheets

(56) References Cited

U.S. PATENT DOCUMENTS

| | | | |
|---|---|---|---|
| 3,705,577 A | 12/1972 | Sierra | |
| 4,020,847 A | 5/1977 | Clark, III | |
| 4,177,797 A | 12/1979 | Baylis et al. | |
| 4,589,412 A | 5/1986 | Kensey | |
| 4,646,738 A | 3/1987 | Trott | |
| 4,729,763 A | 3/1988 | Henrie | |
| 4,732,154 A | 3/1988 | Shiber | |
| 4,781,186 A | 11/1988 | Simpson et al. | |
| 4,781,187 A | 11/1988 | Herrick | |
| 4,790,812 A | 12/1988 | Hawkins, Jr. et al. | |
| 4,819,634 A | 4/1989 | Shiber | |
| 4,842,579 A * | 6/1989 | Shiber | A61B 17/22012 604/22 |
| 4,867,157 A | 9/1989 | McGurk-Burleson et al. | |
| 4,923,462 A | 5/1990 | Stevens | |
| 4,979,951 A * | 12/1990 | Simpson | A61B 17/22031 600/565 |
| 5,192,291 A | 3/1993 | Pannek, Jr. | |
| 5,234,451 A | 8/1993 | Osypka | |
| 5,419,774 A * | 5/1995 | Willard | A61B 17/3207 604/22 |
| 5,507,760 A | 4/1996 | Wynne et al. | |
| 5,507,761 A | 4/1996 | Duer | |
| 5,512,044 A | 4/1996 | Duer | |
| 5,823,971 A | 10/1998 | Robinson et al. | |
| 5,833,704 A | 11/1998 | McCombs et al. | |
| 5,873,882 A | 2/1999 | Straub et al. | |
| 5,876,414 A | 3/1999 | Straub | |
| 5,906,627 A | 5/1999 | Spaulding et al. | |
| 5,922,003 A | 7/1999 | Anctil et al. | |
| 5,935,108 A | 8/1999 | Katoh et al. | |
| 5,947,985 A | 9/1999 | Imran | |
| 6,010,449 A | 1/2000 | Selmon et al. | |
| 6,129,734 A | 10/2000 | Shturman et al. | |
| 6,183,432 B1 | 2/2001 | Milo | |
| 6,238,405 B1 | 5/2001 | Findlay, III et al. | |
| 6,533,749 B1 | 3/2003 | Mitusina et al. | |
| 6,638,233 B2 | 10/2003 | Corvi et al. | |
| 6,733,511 B2 | 5/2004 | Hall et al. | |
| 6,790,204 B2 | 9/2004 | Zadno-Azizi et al. | |
| 7,708,749 B2 | 5/2010 | Simpson et al. | |
| 7,729,745 B2 | 6/2010 | Maschke | |
| 7,905,896 B2 | 3/2011 | Straub | |
| 8,114,106 B2 | 2/2012 | Straub | |
| 8,568,432 B2 | 10/2013 | Straub | |
| 8,628,549 B2 | 1/2014 | To et al. | |
| 8,900,257 B2 | 12/2014 | Straub et al. | |
| 9,687,266 B2 | 6/2017 | Moberg et al. | |
| 9,687,267 B2 | 6/2017 | Zhang et al. | |
| 2002/0058904 A1 | 5/2002 | Boock et al. | |
| 2003/0023263 A1 | 1/2003 | Krolik et al. | |
| 2003/0120295 A1 | 6/2003 | Simpson et al. | |
| 2004/0167553 A1 | 8/2004 | Simpson et al. | |
| 2005/0177068 A1 | 8/2005 | Simpson | |
| 2007/0010840 A1 | 1/2007 | Rosenthal et al. | |
| 2007/0049958 A1 | 3/2007 | Adams | |
| 2008/0045986 A1 | 2/2008 | To et al. | |
| 2008/0051812 A1 | 2/2008 | Schmitz et al. | |
| 2008/0065124 A1 * | 3/2008 | Olson | A61B 17/320783 606/159 |
| 2008/0161840 A1 | 7/2008 | Osiroff et al. | |
| 2010/0049225 A1 | 2/2010 | To et al. | |
| 2010/0312263 A1 | 12/2010 | Moberg et al. | |
| 2012/0179181 A1 | 7/2012 | Straub et al. | |
| 2017/0333060 A1 * | 11/2017 | Panian | A61M 39/06 |

FOREIGN PATENT DOCUMENTS

| | | |
|---|---|---|
| WO | WO-0115609 A1 | 3/2001 |
| WO | WO-0219928 A2 | 3/2002 |

* cited by examiner

THROMBECTOMY CATHETER

CROSS-REFERENCE TO RELATED APPLICATIONS

This application claims the benefit of U.S. Provisional Patent Application No. 62/584,326, filed Nov. 10, 2017, and entitled "Thrombectomy Catheter," the contents of which are fully incorporated herein by reference.

BACKGROUND OF THE INVENTION

1. Field of the Invention

The present invention relates generally to medical devices and methods. More particularly, the present invention relates to devices and methods for disrupting, collecting, and removing occlusive material from blood vessels and other body lumens.

Many diseases cause an undesirable buildup of occlusive material. Thrombosis and atherosclerosis are common ailments that result from the deposition of thrombus and clot on the walls of blood vessels. When hardened, such deposits are commonly referred to as plaque. These deposits restrict blood flow and pose a risk of fragmenting into the blood stream. If this occlusive material travels to the heart, brain, or lungs, the event can be fatal.

An example of one such disease state is Deep Venous Thrombosis (DVT), where blood clots form in the deep (non-superficial) veins of the body, typically within the legs. DVT is commonly characterized by the build-up of large volumes of tough, chronic clot which impedes venous flow. Every year in the U.S. about 700,000 people are diagnosed with DVT and approximately 200,000 people die of pulmonary embolism, a complication of DVT. Sixty to seventy percent of patients with DVT eventually experience post thrombotic syndrome (PTS) as a result of damage to the venous valves secondary from the cellular response and from overgrowth caused by the thrombus. The damage characteristic of PTS can also lead to chronic venous diseases (CVD) caused by Chronic Venous Insufficiency (CVI). Over 7,000,000 in the U.S. suffer from CVI, a painful and debilitating disease that affects the superficial and deep veins of the legs. Complications associated with CVI include varicose veins, bleeding, ulcerations, severe swelling, deep vein thrombosis, and pulmonary embolism. These diseases are reoccurring and can proliferate into interrelated diseases. The risk for delayed reoccurrence is common across disease states that include the buildup of thrombus, plaque, or other occlusive material. As such, there exists a need for an effective debulking treatment that not only addresses the complication but also prevents the proliferation and reoccurrence of further, related complications.

The removal of occlusive material from blood vessels and other body lumens has commonly been approached through treatments based on drug administration, filter implants, and catheter based removal. Although many disadvantages of the prior art are neither obvious nor well known, all methods currently in use suffer from one or more disadvantages.

Anticoagulant drugs, such as Heparin, are the most commonly prescribed treatments for DVT. The administration of anticoagulants prevents the clot from growing and relies on the body's lysing processes to eliminate the clot. This process is expensive, slow acting, not effective against large or complete occlusions, and risks residual clot entering the blood stream to cause venous damage elsewhere, which can lead to PTS.

Thrombolytic drug infusion directly into the clot is an alternative approach. Thrombolytics such as tPA work to actively break down the fibrin backbone of the clot. This destroys the clot more quickly, but introduces additional cost, risks clot fragmenting into the blood stream, and involves a high risk of hemorrhage, which can be fatal. The risk of bleeding complications typically necessitates administration of the drug in a hospital setting where the patient is held overnight or for several days for observation. For many patients, such as those whom have recently under gone surgery, have a high risk for bleeding, or are pregnant, the risk of hemorrhage makes them ineligible to receive thrombolytic drugs.

Thrombus filter implantation is an additional method of treatment. These filters are surgically implanted, typically into the inferior vena cava. Filters function to capture clot and then allow the body's lysing processes to eliminate the clot. Although the use of these filters can greatly reduce the likelihood of clot fragments traveling to the heart or lungs, they often require the use of anticoagulant drugs in concert and therefore entail all the complications described above. Furthermore, poor rates of physician follow-up and patient compliance result in a low percentage of filters ever being retrieved. Unretrieved filters are a common cause of inferior vena cava thrombosis. Filters may also clog, restricting blood flow and in some cases causing full occlusion. Thus, thrombus filters can cause the very problems they are intended to solve.

Catheter-based interventions present an alternative treatment method. Catheters or catheter-based devices are percutaneously introduced into blood vessels and are maneuvered into direct contact with a target substance. For newly formed thrombus or unadhered and small plaque, the substance may be removed through a catheter via aspiration, mechanical capture, or other means. This approach has the benefit of quickly removing the target substances and the benefit of leaving behind little residual material, which could otherwise lead to reoccurrence or proliferation of related diseases. However, the limitations on the type and volume of occlusive material which can be successfully removed make it a non-viable approach to many disease states, such as DVT which typically involves large, tough thrombus burdens.

Some catheter-based devices include rotating blades, high pressure water jets, laser ablation, or other aggressive means of breaking up the target material. Such methods are common in atherectomy-specific tools where the occlusion is formed by well-adhered plaque. Many such devices suffer from at least one of two serious shortcomings. Firstly, the methods of removing targeted substances once the substances are fragmented are either ineffective or non-existent. Even in devices that do possess a debulking strategy, these devices often include small lumens that are prone to clogging or inefficient pressure gradients that fail to pull dislodged clot or plaque into the system. If not removed, dislodged clot or plaque is released into downstream blood vessels and poses a risk for further complications. Secondly, the more aggressive devices, such as those using rotating blades to fragment tough clot or plaque, are often exposed within the body lumen in a manner that risks damaging the vessel wall.

Such systems and techniques, however, frequently suffer from disadvantages and shortcomings such as vessel damage, clot fragmentation, blood loss, prolonged surgery, and/or catheter clogging.

For the reasons discussed above, there has existed a long felt and unmet need for methods and apparatus that remove a wide range of occlusive materials, including at least clot, thrombus, and atheroma, quickly and safely. In particular, it would be desirable to provide systems and methods which remove such occlusive substances quickly, which safely incorporate apparatus for fragmenting the occlusive substances, which enhance digestion of the occlusive substances, which utilize aspiration to limit release of the fragmented substances, and which can be safely introduced into a patient's vasculature. The invention herein described and claimed, and its various embodiments, present solutions that satisfy at least some of these objectives.

2. Background of Related Art

Atherectomy catheters having rotating, cylindrical cutting blades are described in U.S. Pat. Nos. 4,781,187; 5,507,760; 9,687,266 and 9,687,267. Other thrombectomy and atherectomy catheters and protocols are described in U.S. Pat. Nos. 5,419,774, 5,192,291, 6,010,449, 6,638,233, 8,628,549 and 4,177,797.

SUMMARY OF THE INVENTION

A thrombectomy catheter for use in a subject's vasculature includes a rotating and axially movable, cylindrical cutting body. The thrombectomy device is especially suited for removal of tough, chronic thrombus such as that which is found in cases of Deep Vein Thrombosis. We have developed a catheter-based device which relies on automated actuation in order to facilitate rapid thrombus removal. The automated motion is housed in a handle that is operated by the physician user. The systems and methods disclosed herein remove target substances quickly, safely house an apparatus for fragmenting target substances, optimizes thrombus digestion, utilizes aspiration to limit release of fragmented clot, and can be safely introduced into a patient's vasculature.

The device includes a catheter containing a cutting tip affixed to a mandrel. Rotational motion and linear actuation are simultaneously applied to the cutting tip mandrel, resulting in the mastication of thrombus within the catheter. The system relies on the use of aspiration via the Penumbra pump to draw thrombus into the catheter and facilitate debulking once the thrombus mass has been broken up by the rotating cutting tip. An attached handle provides the source of the rotational and linear motion, as well as the connection between the catheter, cutting tip mandrel, and aspiration source. A device made according to the design disclosed herein would not include "raised elements" or an "abrasive" surface in addition to the cutting edge.

In a first specific aspect, the present invention provides a system for removing of one or more target substances, such as thrombus, clot, atheroma, plaque, and the like, from a body passageway, such an artery, a vein, or other blood vessel or body lumen. The system comprises a catheter having a lumen, a proximal end, and a distal end. The proximal end of the lumen is typically configured to be fluidly coupled to an aspiration source, such as a pump or other vacuum source. A cutting member having a leading cutting edge is disposed in the lumen and configured for axial motion, typically reciprocation, within the lumen between a proximal-most position and a distal-most position. An opposing surface is disposed within at a distal location in the lumen, and the leading cutting edge of the cutting member is configured to contact the opposing surface and to shear target substance disposed between the leading edge and the opposing surface when the cutting member is positioned in the distal position. The cutting member and the opposing surface are typically configured to fragment a targeted substance into fragments having discreet and relatively uniform volumes upon axial motion of the cutting member.

In specific embodiments, the cutting member is further configured for rotation and/or rotational oscillation, and the system may further comprise at least one motor coupled with the cutting member, wherein the at least one motor is configured to impart at least axial motion and often both rotational motion and reciprocal axial motion to the cutting member. The at least one motor is may be configured to rotate the cutting at a speed of up to 3000 RPM, typically in a range between 1000 RPM and 3000 RPM. The at least one motor may be further configured to axially reciprocate the cutting member at a frequency of up to 6 Hz, typically in a range from 3 Hz to 6 Hz.

The cutting member is typically cylindrical with a leading cutting edge where the leading cutting edge will often be serrated with cutting teeth. The opposing surface may comprise a cone disposed distal to the cutting member, wherein the cutting member is configured so that the leading cutting edge of the cutting member engages the a conical surface on the cone as the cutting member is advanced fully in a distal direction. A base of the cone may be attached to a distal end of the catheter and a pointed conical tip of the cone may be directed proximally. In some instances, the cone may be configured for rotational motion so that it can accommodate rotation of the cutting blade.

In further embodiments, the catheter includes an atraumatic tip. The atraumatic tip may comprise a metallic backbone and a polymeric material. The metallic backbone may comprise a preselected angle or arc, or may comprise a wound spring.

In a second specific aspect, the present invention provides a system for removal of one or more substances from a body passageway. The system comprises a catheter having a lumen, a proximal end, a distal end, and a sidewall, where the sidewall comprises an aperture disposed near the distal end of the catheter. A cone having a base and a tip is positioned at the distal end of the catheter, and the base of the cone is oriented toward the distal end of the catheter while the tip of the cone is orientated toward the proximal end of the catheter. A distally facing cutting member is disposed in the lumen of the catheter, typically adjacent to aperture, and the cutting member is configured for reciprocal axial translation in both a distal direction toward the cone in a proximal direction away from the cone.

In specific embodiments, this second system may further comprise a motor configured to impart axial motion to the cutting member. The cutting member may be further configured for rotation and/or rotational oscillation, and the system may further comprises a motor configured to imparts both axial and rotational motion to the cutting member. An aspiration source may be placed in fluid communication with the catheter, and the cutting member is configured to rotate at a speed of up to 3000 RPM. The cutting member may be further configured for axial translation at a frequency of up to 6 Hz.

In further specific embodiments, the cutting member may be cylindrical with a leading cutting edge, where the leading cutting edge is serrated with cutting teeth. The cone typically has a conical surface disposed distal to the cutting member, and the cutting member is typically configured so that the leading cutting edge of the cutting member engages the conical surface on the cone as the cutting member is advanced fully in a distal direction.

In a third specific aspect, the present invention provides a method for removing a target substance, such as thrombus, clot, atheroma, plaque, and the like, from a body passageway, such an artery, a vein, or other blood vessel or body lumen. The method comprises providing a catheter including a lumen and a cone and a blade disposed in a distal end of the lumen. The distal end of the catheter is advanced to a target substance in the body passageway, and aspiration through the lumen is initiated to draw the target substance between a cutting edge of the blade and an opposing conical surface of the cone. The target substance is then removed by axially reciprocating the blade so the blade engages the target substance and shears the target substance against the opposing conical surface of the cone.

In specific instances, the blade is rotated in addition to being reciprocated to enhance shearing of the target substance. The target substance may be penetrated by a conical tip on the cone as the blade is axially reciprocated to immobilize the target substance as it is being sheared and to further enhance fragmentation of the target substance to facilitate aspiration and removal. Removal is typically affected by initiating aspiration through the lumen to draws the target substance though an aperture in a sidewall of the catheter and then into a space between the cutting edge of the blade and the opposing conical surface of the cone.

BRIEF DESCRIPTION OF THE DRAWINGS

An object of the present invention is to provide an improved apparatus and method for removing a target object from a body passageway. A further object of the present invention is to provide an improved apparatus and method for removing a target substance from a body passageway, which is particularly useful for removing blood clots quickly and safely.

These and other features, aspects, and advantages of the present invention will become better understood with regard to the following description, appended claims, and accompanying drawings where:

DETAILED DESCRIPTION OF THE INVENTION

Figure 1:
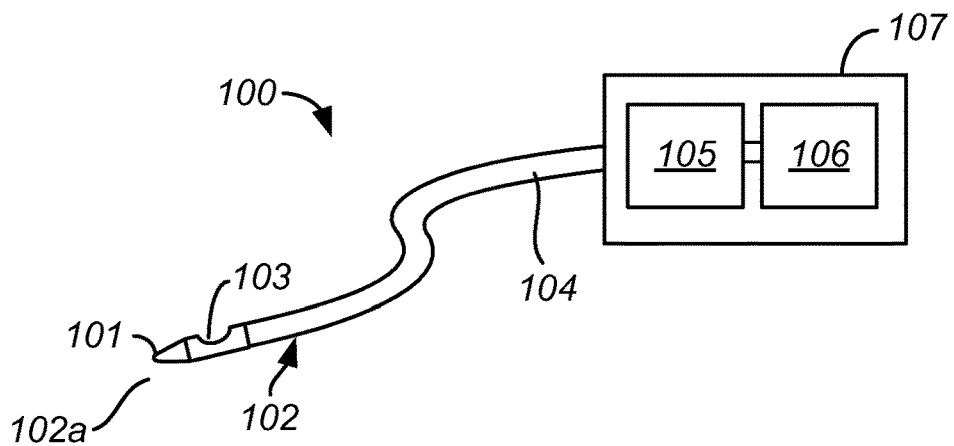
FIG. 1 shows a perspective view of a thrombectomy catheter system in accordance with one embodiment.

In the following detailed description, drawings are referenced that illustrate how specific embodiments of the present invention may be practiced. These embodiments are described in sufficient detail to enable those skilled in the art to practice aspects of this disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

As used herein, the articles "a", "an" and "the" are intended to include both the singular and the plural forms, unless the context clearly indicates otherwise.

As used herein, the term "and" and "or" are understood to include both inclusive and non-inclusive understandings of these conjunctions. For instance, the conjunctions "and" and "or" should be understood as encompassing any of the options independently or any combination of the options in concert, unless the context clearly indicates otherwise.

As used herein, the terms "comprises", "comprising", "includes", "including", or any variation thereof, are intended to reference a non-exclusive inclusion, such that a process, method, article, composition, or apparatus that comprises a list of elements does not include only those elements recited, but may also include other elements not expressly listed or inherent to such process, method, article, composition, or apparatus.

Directional or positional terminology, such as "top," "bottom," "front," "back," "leading," "trailing," etc., is used with reference to the orientation of the figure(s) being described. Because components of embodiments of the present invention can be positioned in a number of different orientations, this terminology is used for purposes of illustration and is in no way limiting. Other combinations and/or modifications of the above-described structures, arrangements, applications, proportions, elements, materials, or components used in the practice of the present subject matter, in addition to those not specifically recited, may be varied or otherwise particularly adapted to specific environments, manufacturing specifications, design parameters, or other operating requirements without departing from the general principles of the same.

As used herein, the terms "distal" and "proximal" are understood as positional referents. Objects, elements, and components are "proximal to" or "distal to" one another on the system. "Proximal" refers to a direction toward the system controls and the operator along the path of the catheter system, and "distal" refers to the direction away from the system controls and the operator along the path of the catheter system toward or beyond a terminal end of the operating head.

As used herein, the term "dynamic" refers to a state opposed to, or opposite to, a static state. For instance, a dynamic shearing force oscillates between a high and low force. Furthermore, the term "dynamic" indicates a measured approach; an approach designed to optimize the desired results. In one embodiment, an algorithm may determine or adjust in real-time the oscillation of a dynamic state to optimize results.

As used herein, the term "occlusion" refers to both partial vessel occlusion and complete vessel occlusion. Examples of partial vessel occlusion include a vessel that is narrowed by hardened substances, such as plaque. Additionally, as used herein, the "complete" removal of an occlusion is understood as an effective removal of thrombus. Occlusive material may escape removal, while a person having ordinary skill in the art would characterize the removal as complete in that the device has restored patency to the vessel.

As used herein, the terms "blade" and "cutting member" are understood to include any cutting device that achieves a substantially similar result to a cylindrical blade characteristic of a bore drill or hole saw. The term "blade" refers to both the cutting edge and the supporting cylinder. The term "blade" is understood to include any polyhedral that achieves a substantially similar result. For instance, the blade may have as few as one side; a blade may have three sides, such as in a triangular cylinder, eight sides, such as in an octagon cylinder, or any number of sides above or between these two variations. Alternatively, the shape of the "blade" is not necessarily a shape with even-symmetry but instead may be of a conic shape, n-ellipse shape, or super-ellipse shape. Furthermore, "blade" is not to be understood as limited to solid cylindrical shafts, instead "blade" should be understood as encompassing a cutting edge structurally supported by any framework that satisfactorily maintains the desired shape and rigidity of the cutting edge. For instance, an annular blade supported by a series of pillars, ribbons, or cross-hatched wires (e.g. chicken wire) is understood to fall within the definition of "blade" as used herein. However, as their plain meaning would indicate, a "cutting member" refers to a broader class of cutting instruments than a "blade," and a "cutting member" should be understood as fully including all variations of the "blade" as described above.

As used herein, the term "cone" is understood to include any shape that can engage against the blade or cutting member to a satisfactory degree as the blade either rotates and/or actuates, including anything between a two-dimensional triangular edge and a spherical cone. The term "cone" is also understood to include any juxtapositions of multiple nearly-two-dimensional triangles whose juxtaposed base forms any shape between a rectangle and a circle. Additionally, the cone could be replaced with a flat-face, a spherical surface, or a cylindrical punch and still fall within the scope of this invention. Such shapes may perform sub-optimally, but they are within the spirit and scope of the device's method of clot fragmentation between two, variably positioned non-biological surfaces. The cone may optionally be comprised of a metal alloy, a ceramic, or a polymer. While cones having pointed apices or tips are illustrated and will be commonly employed, truncated and other conical geometries may also find use.

As used herein, an aspiration source may refer to any device that supplies a negative pressure gradient. The source of negative pressure could be a vacuum pump, peristaltic pump, a diaphragm pump, a piston-based pump, a high-speed water jet disposed at a proper angle and orientation to create a favorable negative pressure gradient, or a simple syringe. All variations are understood to fall within the scope and spirit of the present invention.

Some aspects of the present subject matter may be illustrated via functional block components and various processing steps. Such functional blocks may be realized by any number of techniques, technologies, and methods configured to perform the specified functions and achieve the various results. The systems described are merely exemplary applications. Furthermore, any particular order to the functional blocks is merely illustrative of one possible order for the steps described. It will be appreciated that methods described and illustrated may be performed in any order and/or simultaneously without departing from the scope of the present invention, disclosure, or claims.

Referring now to the drawings in detail, there is depicted a preferred embodiment of the apparatus of the invention, which is useful for the removal of objects that restrict healthy flow such as thrombus, blood clots, atheroma, gallstones, kidney stones, purulent material fluid, polyps, cysts or other obstructive matter from body lumens, such as blood vessels, ureters, bile ducts, or fallopian tubes. The numerals assigned to each element indicate the figure being referenced. For instance, numerals in the 100's reference FIG. 1 and numerals in the 400's reference FIG. 4.

FIG. 1 illustrates a perspective view of one embodiment of the present invention's thrombectomy catheter system 100. System 100 includes specialized catheter 102 attached to base unit 107 that houses motorized components that are operated by a user to effectuate working internal components (not visible in FIG. 1) of specialized catheter 102 of system 100. A distal end 102a of the catheter 102 is inserted into a vein, artery, or other passageway, advanced to a treatment site, and then deployed to mechanically disrupt, fragment, and aspirate a target substance(s) from the passageway. An atraumatic tip 101 is disposed at a distal end of catheter 102. Tip 101 reduces the risk that the passageway will be damaged by the insertion and placement of catheter 102. An aperture 103 is located near the distal end of catheter 102. Aperture 103 permits substance(s) from the patient's body to enter an aspiration lumen formed in the catheter 102. A proximal end 104 of catheter 102 is coupled to a motor 105 that provides rotational and/or reciprocal axial motions to internal components of catheter 102, as discussed in greater detail below. The proximal end 104 of catheter 102 is in fluid communication with an aspiration source, such as pump 106, that provides a negative pressure gradient (e.g. vacuum suction) which draws and the target substance(s) through aperture 103 and into the aspiration lumen of the catheter 102. Other known aspiration sources may be used within the scope of this invention. Together, the negative pressure gradient and the mechanical fragmentation ensure the efficient and effective removal of substances from the body. In alternative embodiments, system 100 may include more than one pump or valve in fluid communication with system 100. Such pumps and valves may provide or remove fluids in a way that alters the pressure within system 100. System 100 may be controlled by an ergonomically shaped handle (not pictured in FIG. 1) that houses motor 105 and either houses or is in fluid contact with pump 106. This allows the user to easily control and manipulate system 100.

Figure 2:
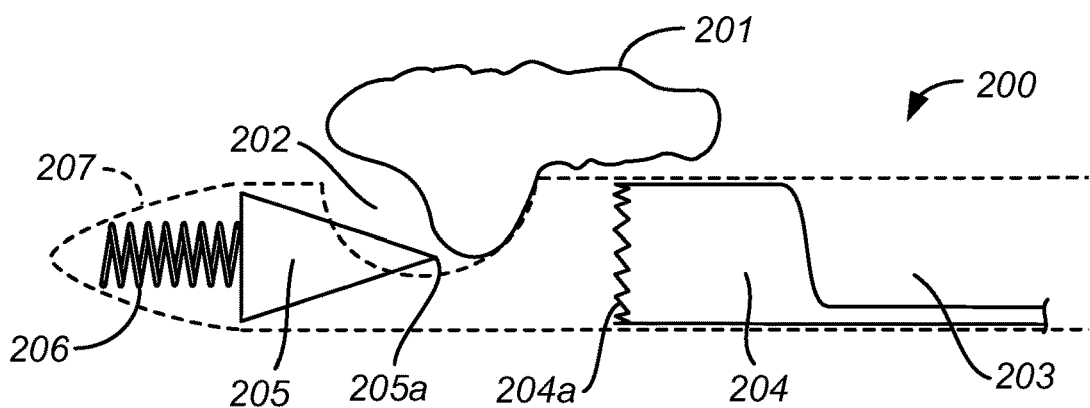
FIG. 2 shows a side, transparent, detail view of a distalmost segment of a system embodiment according to the invention.

FIG. 2 illustrates one embodiment of a distal region 200 of a catheter constructed in accordance with the principles of the present invention. The distal region 200 is shown as transparent in order to facilitate an understanding of its internal components. Distal region 200 has an aperture 202 configured to draw in thrombus or another target substance 201, as shown partially within aperture 202. The target substance 201 is drawn into aperture 202 by an aspiration source (such as pump 106 in FIG. 1) that provides a negative pressure gradient within a lumen 203 of the catheter. An opposing surface in the form of cone 205 is located distal to aperture 202, where a tip 205a of cone 205 is pointing proximally. In alternative embodiments, an opposing surface or cutting surface may be in the shape of a bulb or other suitable form. In some embodiments, a portion of cone 205 may be visible through aperture 202, even without the benefit of a transparent illustration. Also visible in FIG. 2 just proximal of aperture 202 is a blade 204. Blade 204 is typically cylindrical and configured to be rotated and/or to be translated in both axial directions. Blade 204 may be further configured to circumscribe, superimpose, surround or otherwise mate with a cone 205, where the cone may have a diameter at or near its base which approximates an inner diameter of a leading, cutting edge 204a of the cylindrical cutting blade 204. The cutting edge 204a of blade 204, in some embodiments, may contact an opposing surface of cone 205 as the blade is brought axially forward, as shown in FIG. 6C discussed below. Alternatively, an interior surface of the distal region 200 of the catheter may be configured to present a transverse flat or other opposing surface (not illustrated), and the cutting edge of blade 204 may contact this opposing surface when blade 204 is moved to its most distal axial position. During use of a catheter having distal region 200, the substance 201 will be broken apart or fragmented by shearing or other interactions between blade 204 and the opposing surface, or cone 205. Fragments of the target substance 201 are drawn into and through lumen 203 to a proximal region of the catheter where they may be removed from the body of the patient.

As will be discussed in greater detail below, as a substance is drawn by an aspiration source into aperture 202 and the blade 204 is distally advanced (usually while simultaneously being rotated or rotationally oscillated) to the opposing surface of cone 205, the substance is caught between and is subjected to shearing forces (see FIG. 9A-D) that fragment the substance. The resulting fragments are then drawn by the aspiration source into lumen 203 of catheter 200. The cooperative interaction of these components and elements allow system 100 to ingest large substances. The substances are broken up within the system and ingested, while aspiration ensures that minimal, if any, residual substance is permitted to escape evacuation. Once the substance 201 or portion thereof is inside lumen 203 of the catheter, aspiration draws the substance through the lumen and into a collection chamber (not pictured).

A soft, atraumatic distal tip 207 allows for the safe advancement of the device through the diseased vessel. A forward or leading edge of the cutting blade 204 is typically serrated or otherwise configured to promote cutting of the target substance as the blade is advanced and optionally rotated or rotationally oscillated and further configured to promote shearing of the excised portion of the target substance from the remaining mass of target substance as the leading edge engages the cone or other surface within the distal region 200 of the catheter.

The aperture 202 is typically formed as a "side window" in the distal region 200 of the catheter, and the cutting blade 207 may be advanced and retracted to adjust the size of a gap between the cutting body and the distal end of the window. Aspiration pulls the target substance, such as clot material, to the open window, and the rotating cutting blade 207 fragments the clot as it enters the window. A motor which rotates or rotationally oscillates the cutting blade will typically be attached to a proximal end of the catheter, as shown for example in FIG. 1, and may be housed in an ergonomically designed handle. The aperture may be formed in a separate structure at the distal end of the catheter, such as in a separate housing. For example, the separate housing may be a metal or rigid polymeric tube having the aperture formed therein.

The distal end of the distal region of the catheter is typically closed and has a cone 205 with a conical tip 205a attached thereto. The conical tip 205a is tapered or pointed and faces in a proximal direction. The leading edge 204a of the cutting blade 204 is received over the cone 205 as the blade is advanced distally to cut target substances received through the aperture 202. Shearing action of the rotating cutting body against the outer surface of the cone, and advancement and retraction of the cutting body over the cone, further macerates the clot.

The device is intended to be used by a physician trained in interventional techniques. In some instances, an assisting technician may operate the handle while the physician drives the catheter.

FIG. 2 further illustrates a spring 206 secured to the distal end of the catheter and covered in polymer to form the soft, atraumatic tip 207. In alternative embodiments, the spring 206 of the atraumatic tip may be replaced with an alternative metallic backbone (being either a metal or metal alloy). For instance, the atraumatic tip may achieve a tapered, gradual stiffness profile by utilizing a pine tree shape, a rod with a sphere, oval, cube, cone, or conic profile on the distal tip, a spring with multiple and varied wind diameters, a spring with multiple, varied pitches, or a hypotube with numerous laser cuts. In alternative embodiments, the metallic backbone may be shaped to have a bend or arc. Such a shape assists with selecting the desired vasculature at juncture points. The metallic backbone ensures that the catheter tip maintains a shape important to its function, while also providing the flexibility necessary for the delicate areas the apparatus traverses. This novel soft, atraumatic tip 207 ensures that the distal edge of catheter 200 can enter the passageways of the body without causing damage to the patient. This tip improves on prior art systems that utilize a polymeric tip by allowing a greater degree of flexibility while still returning to the desired shape absent external pressure. Additionally, this tip improves on prior art by allowing a secure metal-on-metal connection between the catheter and the atraumatic tip. This feature avoids the issue of losing the tip within the patient during surgery, a serious issue that has occurred with prior art devices. In alternative embodiments, the atraumatic tip has a lumen with a valve on the distal tip, which allows a guidewire to pass through while maintaining a vacuum seal in its absence. In further alternative embodiments, a second lumen coextends with the catheter and houses a guidewire. Alternatively, the guidewire may extend within the lumen of the catheter and exit from the catheter's aperture.

Figure 3:
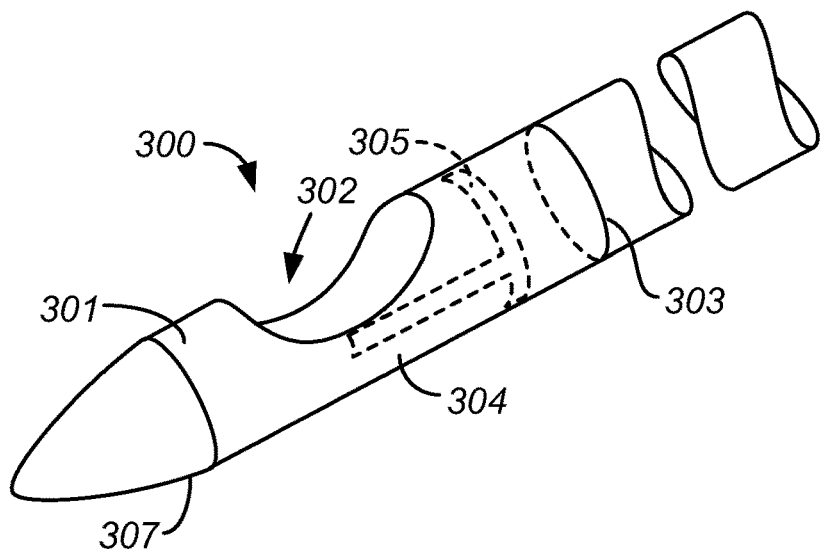
FIG. 3 shows a perspective detail view of a component disposed at the distal end of an embodiment according to the invention.

FIG. 3 illustrates an alternative distal region 300 of a catheter constructed in accordance with the principles of the present invention. Catheter 300 has a distal edge 301. Onto distal edge 301 atraumatic tip 307 is optionally attached. Distal region 300 has an aperture 302. Aperture 302, as shown in this embodiment, is only illustrative of one possible shape and is not meant to be restrictive in any manner. In alternative embodiments, the aperture may be any shape that serves as a means of ensuring structural integrity, while also allowing large substances to at least partially enter. For instance, the aperture may have many openings with one or more sidewalls providing structural integrity between each individual aperture. The aperture may have any one of a square shape, a triangular shape, a circular shape, an elliptical shape, an eye-lid shape, or any shape in-between. While in use, target substances are drawn from the passageways of the body into aperture 302 by a negative pressure gradient force supplied by an aspiration source in fluid communication with a proximal end of the catheter (not visible in FIG. 3). The lumen 303 of the catheter lumen is shaped cylindrically and includes a sidewall 304. The distal catheter region 300 will optionally include a section of radiopaque material. FIG. 3 illustrates a T shaped radiopaque marker 305. The radiopaque marker may be of an L or T shape that outlines a portion of the aperture, may be formed of multiple L or T shapes, and may wrap around the entire circumference of the catheter as a complete band or a C shape.

Alternatively, the radiopaque marker may be shaped in the form of a dot near a cross placed near the system's aperture. The radio opaque material may comprise a metal selected from the group consisting of platinum, gold, and similar dense alloys. This will allow the attending physician to easily view the distal end of the catheter 300 as it is inserted into and maneuvered within the patient.

Figure 4:
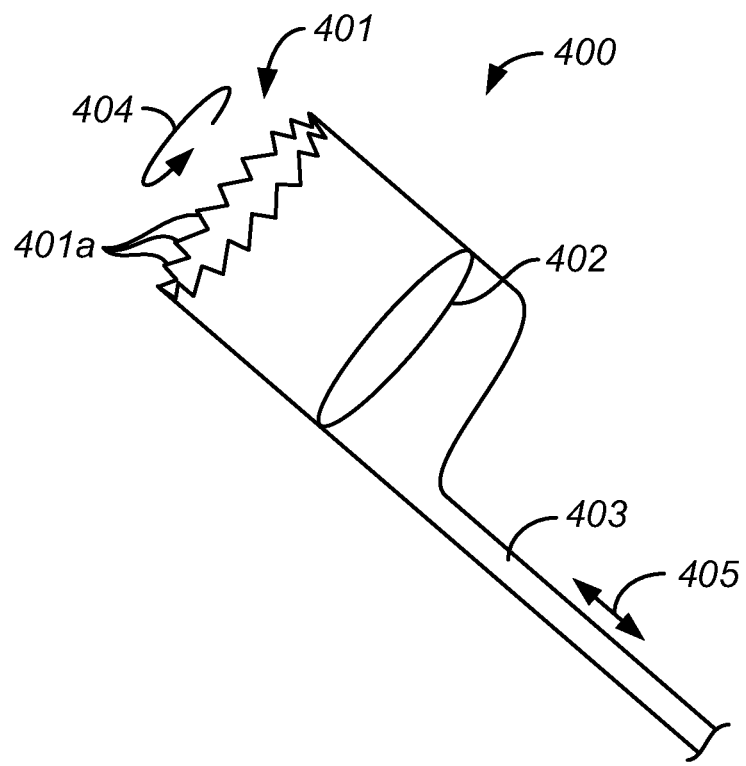
FIG. 4 shows a perspective detail view of an internal component of an embodiment according to the invention.

FIG. 4 illustrates one embodiment of a cutting blade 400 that may be used with any of the an exemplary catheters described herein. Blade 400 is shown independently of a specific catheter system so that details of the blade are more readily observed. A leading cutting edge 401 of blade 400 is serrated, having teeth 401*a* that may be of a variable pitch and/or a spiral cut pattern. Alternatively, the teeth 401*a* of the blade may be irregular and may have consistent or inconsistent gaps between teeth to promote variable sheering forces at any given time in the system's operation. In other embodiments, the teeth may be curved and serrated, like shark teeth, or they may be blunted, rounded, or have a sinusoidal profile depending on the physical properties of the substance targeted for removal. Blade 400 may include a cylindrical lumen 402. Alternatively, the lumen of the blade may be of a triangular, rectangular, pentagonal, hexagonal, etc. shape. In alternative embodiments, the blade may have a lumen with a conical shape, an elliptical shape, or a super-elliptical shape. The shape of the blade's lumen will dictate the shape and dimension of the blade's distal edge where the teeth of the blade are located. Blade 400 tapers at its proximal end for attachment to a mandrel 403, which is optionally covered in a lubricous sheath. Alternatively, blade 400 could have a cylindrical or other body that extends the full length of the catheter, whereby the clot or thrombus remains inside the lumen of the cutting structure for the full length of its travel through the catheter. Mandrel 403 is driven by a motor that supplies both rotational (including rotational oscillation) 404 and/or reciprocal axial 405 motions. The motion imposed on the mandrel by the motor will typically be selected to cause the blade 400 to move in a way that promotes fragmentation of the occlusive material.

Figure 5:
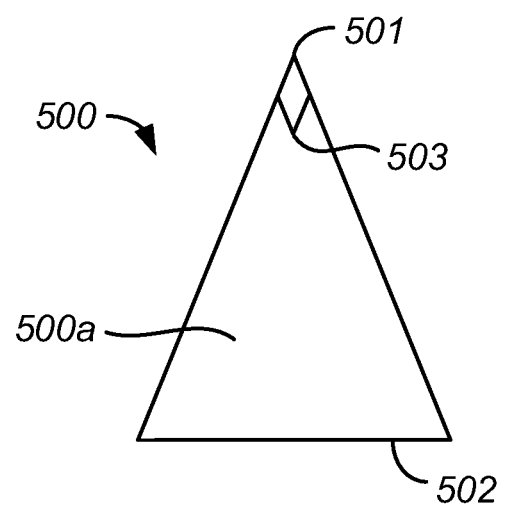
FIG. 5 shows a side view of another internal component, shown in isolation from a system according to the invention.

FIG. 5 illustrates an exemplary cone 500 which provides an opposing surface 500*a* that is useful in a system according to the invention. The cone 500 is shown separately from a catheter so that details of the cone are more readily observed. Cone 500 has tip 501 and base 502, with the opposing surface 500*a* extending between the tip and the base. Tip 501 terminates in a point with an inner angle 503 of between 15° and 120°. In alternative embodiments, the cone may have any number of a number of shapes which are suitable as an opposing surface to a cutting edge of the cutting blade. Exemplary alternatives include an elliptical cone, a cone with a conical base, a cone with a triangular base, or a cone with a base having more than three sides. In one embodiment, cone 500 guides blade 400 through a lumen of a catheter to a distal edge of the catheter. This guiding feature ensures that the blade stays within the lumen and does not emerge from though a cutting aperture, thereby reducing the risk of the blade coming into contact with the vasculature of the patient. The cone also serves as an opposing surface into which a substance, such as a thrombus, is held against while the device's blade rotates and pushes into the substance. The cooperative action of the opposing surface and blade generate shearing forces over and above those seen in the prior art. These additional shearing forces make the device more effective at removing tough clots and more resilient against clogging. In alternative embodiments, the cone has a lumen and is hollow through the center. Such a design allows a guidewire to pass through the system.

Figure 6A:
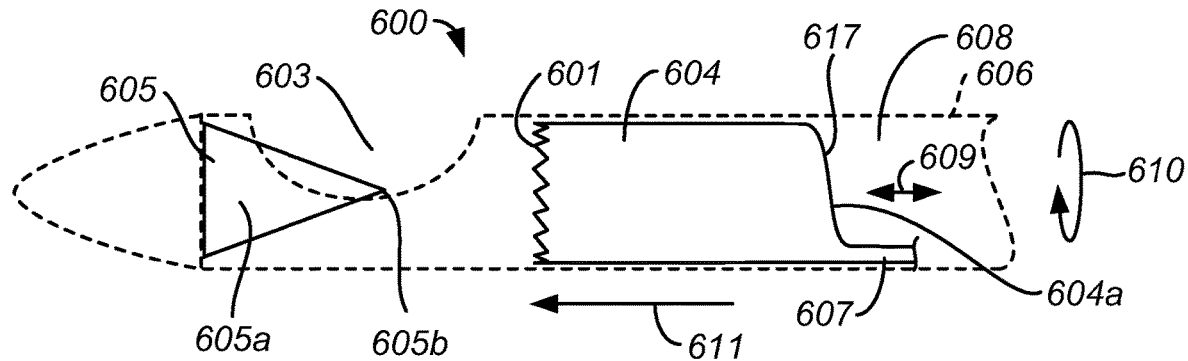
FIG. 6A-6C are transparent views of a distal region of a system according to the invention, and represent a time-lapse illustrating moving components of a system according to the invention.
Figure 6B:
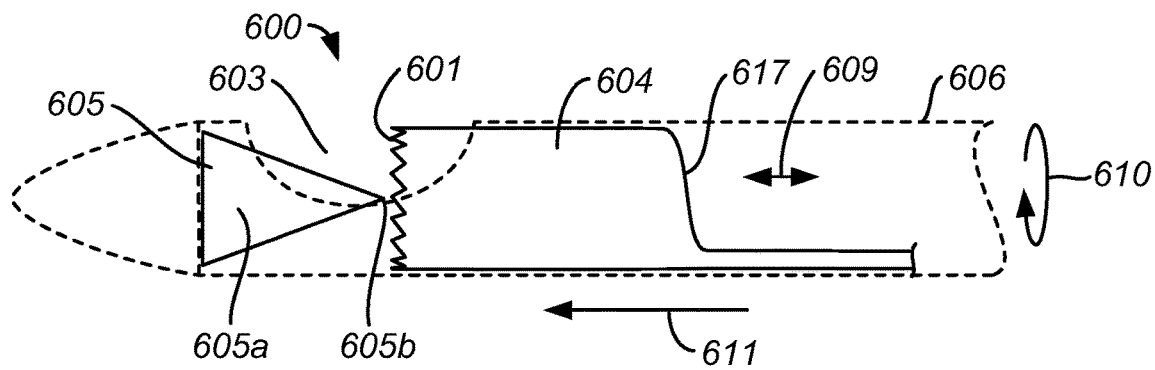
Figure 6C:
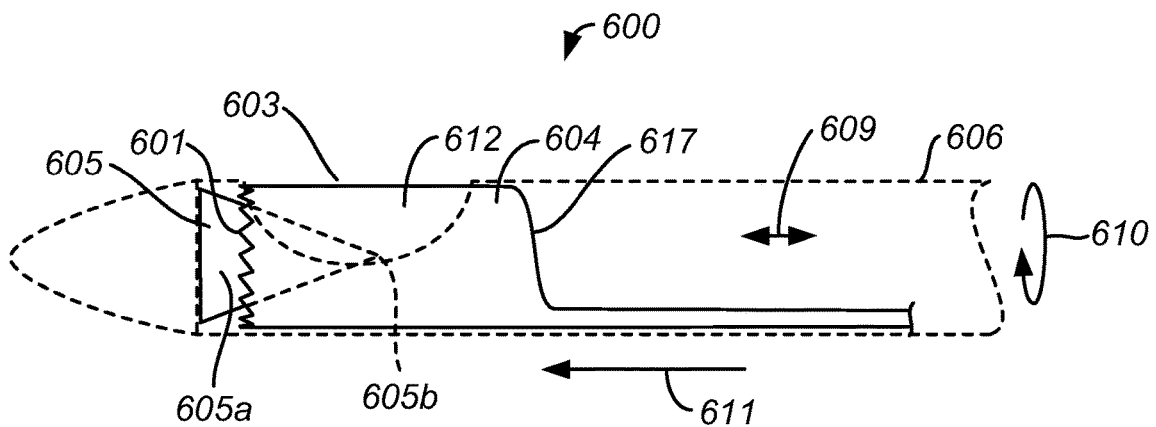

FIGS. 6A-6C illustrate blade advancement and rotation during use of a catheter 606 of the present invention having a distal region 600. The three illustrations show axial advancement and reciprocation of the blade with the various positions of the blade within the catheter providing a desired non-constant shearing and axial forces that serve to shear a target substance and allow for the quick and effective fragmentation of the target into relatively uniformly sized pieces which can be safely removed from the body.

FIG. 6A illustrates a first stage in the progression. The distal end 600 of the catheter 606 is shown as transparent in order to better visualize a cone 605 and a cutting blade 604. The cone 605 and the cutting blade 604 are disposed within a catheter lumen 608. In FIG. 6A, an aperture 603 is shown as completely open. Cutting blade 604 has a forward cutting edge defined by teeth 601 which are shown facing distally as the blade is in its proximal most position where it is disposed inside a lumen 608 of catheter 606 and is not visible in aperture 603. A lumen 617 is formed axially through the cutting blade 604. Cutting blade 604 is axially reciprocatable in opposed distal and proximal directions as illustrated by arrow 609. Cutting blade 604 is also mounted to rotate, as illustrated by circular arrow 610. Cone 605 is shown near a distal end of the distal region 600 of the catheter 606 with its opposing surface 605*a* and tip 605*b* facing proximally. A mandrel or shaft 607 is connected to a proximal edge 604*a* of blade 604. Mandrel 607 is driven by a motor (such as, for example, motor 105 of FIG. 1), that causes rotation and/or rotational oscillation in the direction of arrow 610 (or in an opposite direction in the case of full rotation). The motor may also drive axial reciprocation or single pass movement in the direction of arrow 609 of connected blade 604. In some instances, however, the axial reciprocation could be manually driven, e.g. by a slide on the handle (not shown).

FIG. 6B illustrates a second stage of the progression, in which the moving components of the embodiment are in a second position. In this stage, aperture 603 is shown as halfway closed as blade 604 advances distally according to axial motion 611 within catheter 606 towards cone 605. During axial motion 609, blade 604 may also undergo continuous or dynamic (oscillatory) rotation 610. As blade 604 approaches the opposing surface of cone 605, a substance, such as a thrombus, (not pictured), will be drawn into the lumen by aspiration forces and compressed between the blade and the cone. The distal tip 605*a* cone 605 can pierce a thrombus, while blade 604 advances towards the thrombus to pierce, tear, cut, and otherwise fragment the thrombus.

FIG. 6C illustrates a third stage of the progression. In this stage, aperture 603 is shown as closed 612. Blade 604 has fully advanced distally, according to axial motion 611, and cone 605 is now disposed within lumen 617 of blade 604. At this point, in clinical use, any thrombus or comparable substance between blade 604 and cone 605 would be subjected to the maximum shearing force of the device. The leading edge of blade 604 having teeth 601 closely approaches or directly contacts the opposing surface 605*a* of cone 605, usually near the base of cone 605, to maximally compress and to cut any target substance caught between. The conical tip 605*b* and conical shape of the opposing surface 605*a* of cone 605 pierce and force a portion of a target substance into the teeth 601 and then into lumen 617 of the blade 604. Additionally, the cone 605 acts as a backstop against which the blade rotates. Together, the blade 604 and the cone 605 provide two surfaces between which a portion of the target substance is cut into fragments.

In exemplary embodiments, the diameter of blade 604 may approximate the outer diameter of cone 605 at any point along the exterior of cone 605, up to the largest diameter at the base of cone 605. The optimal diameter of blade 604 may be further determined by the best fit between inner diameter of catheter 606 and an outer diameter of cone 605 near the base of cone 605. Immediately after the configuration illustrated by FIG. 6C, the reciprocal axial motion of the blade 605 would cause the blade to retract to its most proximal position as shown in FIG. 6A before repeating the steps of FIGS. 6B and 6C again, typically at a rate up to approximately 6 Hertz. The interaction between the cone and blade has the benefit of providing a mechanism that works in concert with aspiration. Aspiration causes portions of large substances to partially enter the catheter. The synchronized action of the blade and cone fragment the drawn substance, or piece thereof, thereby allowing aspiration to draw the fragments completely through the catheter to the collection chamber. This synchronized action increases the effectiveness of the system's clot removal features. The clots attacked are drawn in, fragmented, and aspirated through the lumen in repeated cycles.

The present invention utilizes a cyclic function, as illustrated in FIGS. 6A-6C. The cone and blade operate to open and close the aperture repeatedly. The cone and the blade have complimentary shapes that slide into one another to mate and subject anything caught in between to bi-modal shearing forces that result in discreet fragmentation. These two components cause the targeted substance to be digested between two non-biological, non-clot surfaces. While typical prior art devices fragment substances between the surface presented by the device and the surface presented by the vasculature wall behind the target, i.e. between a one non-biological surface and one biological surface. Such a prior art method requires that the fragmenting machinery be housed on the outside of the device, where it risks inadvertently contacting a patient's vasculature. Many aggressive devices designed to treat large, tough, and dense biological substances include rotating blades or abrasive tips, which are exposed on the outside of the catheter where they pose a risk of damaging vasculature. The present invention includes the benefits of these prior art aggressive cutting mechanisms without their respective drawbacks. The present invention achieves this by housing the components responsible for fragmentation safely within the catheter, where it is not at risk of contacting a patient's vasculature.

Figures 7, 8:
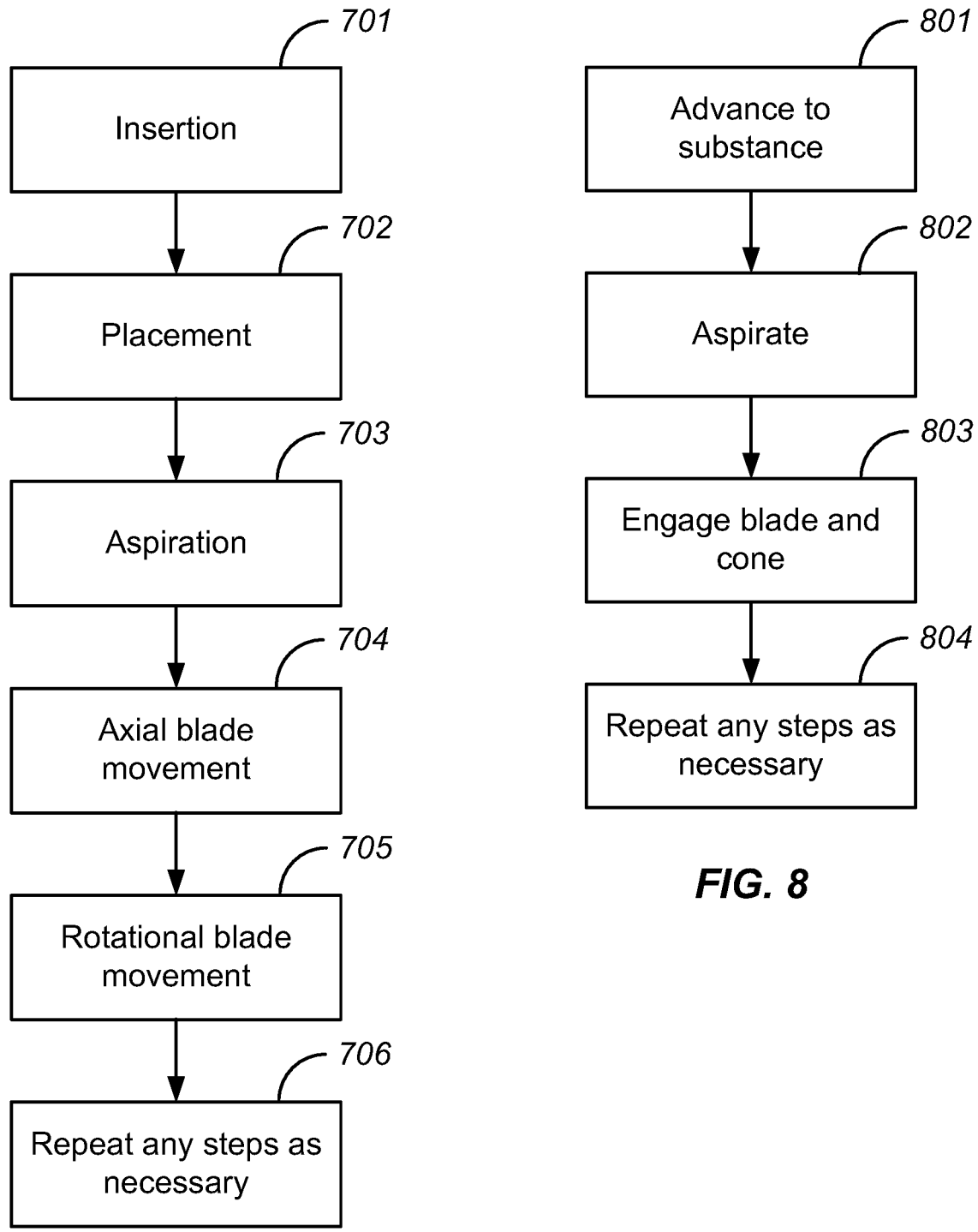
FIG. 7 shows a step-by-step methodology for removing substances from the passageway of a body in accordance with one embodiment.
FIG. 8 shows another step-by-step methodology for removing substances from the passageway of a body in accordance with one embodiment.

FIG. 7 illustrates a diagram of another embodiment of a method for the removal of targe substances from a passageway or body lumen, such as a blood vessel, of a patient. As depicted in FIG. 7, a first step is the insertion 701 of a catheter within a passageway of the patient. A second step is the placement 702 of the catheter in the appropriate position so that the catheter comes within close proximity of a targeted substance(s). A third step is to aspirate 703 so that the substance(s) is drawn towards an aperture of the catheter. A fourth step is to cause reciprocal axial movement in a blade 704 in order to pinch, shear, and otherwise tear off a substance or portion thereof. A fifth step is to cause rotational movement in the blade 705 in order to shear, cut, rip, and otherwise tear off a substance or portion thereof. A sixth step is to repeat any of the other steps as necessary 706. Tough, calcified, or other wised hardened deposits or plaques may require repeated catheter treatments 702 as portions of the substance are evacuated. In addition, the move towards additional portions of the target substance will require repeating aspiration steps 703 and/or blade movements 704, 705. It should be appreciated that these steps can be skipped, performed in any order, performed simultaneously, or include intervening steps and still fall within the scope of the present invention and its equivalents.

FIG. 8 illustrates a diagram of another embodiment of a method for the removal of substances from the passageways of a patient. As depicted in FIG. 8, a first step is to advance a catheter to the substance 801 that is intended to be evacuated. A second step is to aspirate 802, so that a substance(s) is drawn into an aperture of the catheter. A third step is to engage a blade and cone 803 so they come together and move apart at a particular or variable frequency while also employing rotational motion. A fourth step is to repeat any steps as necessary 804. Again, it should be appreciated that these steps can be skipped, performed in any order, performed simultaneously, or include intervening steps and still fall within the scope of the present invention and its equivalents.

Figure 9A:
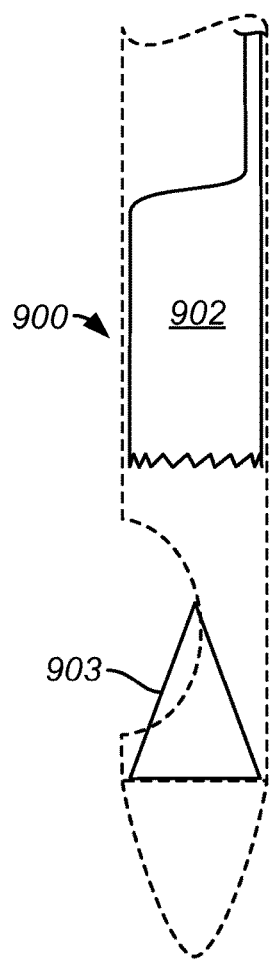
FIG. 9A-9D illustrate an example of axial based shearing forces and the relatively uniform fragments those forces generate in an embodiment of the invention.
Figure 9B:
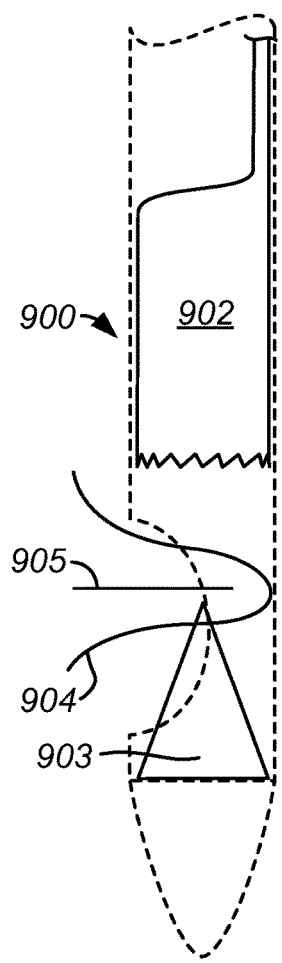
Figure 9C:
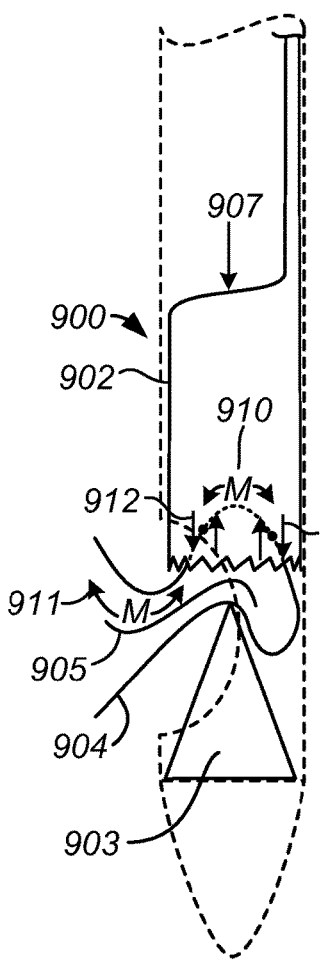
Figure 9D:
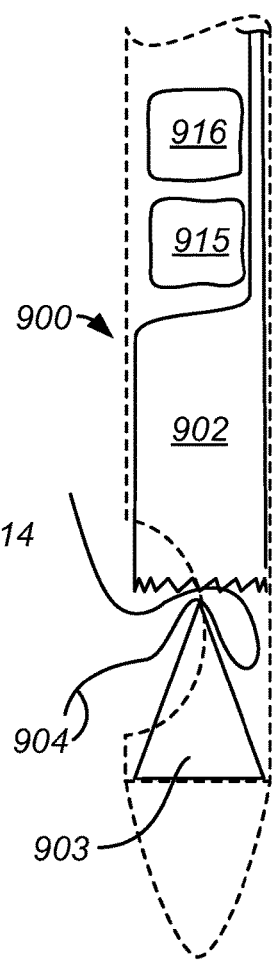

FIGS. 9A, 9B, 9C, and 9D show an embodiment of the present invention in a vertical orientation to illustrate an example of some axial shearing forces that a substance, such as a thrombus or clot, undergoes within a system according to the present invention. FIG. 9D shows the relatively uniform fragmentation that the cyclic nature of the axial shearing causes.

FIGS. 9A and 9B illustrates a system 900 at a first point in time, when system 900 is in a first configuration, prior to axial compression of thrombus 904, and FIG. 9C illustrates system 900 at a second point in time, when system 900 is in a second configuration, during axial compression of a thrombus. For clarity, not all features of a system according to the invention are included in FIGS. 9A, 9B, 9C, and 9D. System 900 includes blade 902 and opposing surface, or cone 903. In FIGS. 9A and 9B, blade 902 and cone 903 have not yet come into contact with a soon-to-be trapped substance, which in this example shall be referred to as clot 904. Within clot 904 a fitted line 905 showing a linear approximation extends through the center of the clot. Prior to any deformation caused by blade 902 and cone 903, fitted line 905 resembles a straight line. This line is meant to indicate the axial forces being applied to the clot at this point in time.

Turning to FIG. 9C, a force 907 has pushed blade 902 into clot 904. The force applied to blade 902 is transferred to clot 904 which is thereby deformed. The clot 904 often deforms in a shape 905 which approximates sinusoidal, as shown in FIG. 9C. Of course, such a sinusoidal deformation results from only a portion of the axial forces experienced by the clot. This narrow focus permits a clear illustration of an exemplary example of the some of the major axial shearing forces a clot will be subjected to between a blade and cone.

Starting from the left, clot 904 experiences a downward force, illustrated by the left side of the sinusoidal approximation (fitted line 905). Above the left side of the sinusoidal approximation on clot 904 a hogging moment 911 is shown by a "−M" and two upward-curved arrows. Above the right side of the sinusoidal approximation a sagging moment 910 is shown by a "+M" and two downward-curved arrows. The arrows of these moments mirror a sinusoidal wave, because the left side of the clot experiences a downward force from blade 902 while the center of the clot (or the right side of sinusoidal approximation) experiences an upward force from the cone. These forces act in opposite directions and therefore cause a shearing force in between. This shearing is shown on clot 904 by two half-headed arrows 912 indicating a counter-clockwise shearing force. On the other side of the clot 904 another shearing forces is shown 913 that indicates a clockwise shearing force. A person having ordinary skill in the art can appreciate upon reflection that a clot caught in such a situation would experience a variety of additional shearing forces similar to those detailed. For instance, this two-dimensional sinusoidal approximation would form a plane if rotated 360 degrees. The forces described in reference to points on the two-dimensional illustration could then be described as a ring of forces. This ring of forces more accurately represents the type of axial forces the clot is subjected to.

The utilization of axial shearing forces in this manner is novel to the field of devices and methods for disrupting, collecting, and removing occlusive material from blood vessels and other body lumens. Other catheters utilizing rotating blades are not benefiting from the axial shearing. This axial shearing is particularly beneficial because it enables a bi-modal shearing force which is substantially more effective at disrupting the structure of the target substance. The bi-modal shearing force combines rotational and axial cutting to enable complete and controlled fragmentation.

FIG. 9C illustrates the axial shearing force, but not the rotational shearing force. As clot 904 is trapped between blade 902 and cone 903, blade 902 rotates and imparts a rotational shearing force on the clot 904. The blade side of the clot 904 is sheared as to the opposite side of the clot, which at least partially resists the rotational force because of the cone's pressure. Pressure to turn on one side and a resistant force on the other causes a shearing of the material between as the individual fibers of the clot begin to slide past one another. The inside of the clot experiences a rotational shearing force across the entire length of the blade's teeth (not pictured). The combination of this rotational shearing force and the axial shearing force (bi-modal shearing) serves to efficiently and effectively fragment and digest even the toughest clots.

FIG. 9D shows the discreet and relatively uniform fragmentation that the cyclic nature of the axial shearing causes. The axial motion of cutting member 902, which ultimately places the cutting edge of cutting member 902 into contact with cone 903, causes the fragmentation of clot 904. As cutting member 902 moves distally, clot 904 may be sliced along perforated line 914. This slicing creates a discreet and relatively uniform fragment, which is then immediately aspirated. As the cutting member fragments the clot, the fragment generated is aspirated through the cutting member's lumen in a proximal direction. The relatively uniform fragments 915 are then further aspirated in a proximal direction 916 within the catheter's lumen. This fragmentation occurs within the catheter's lumen, and thereby reduces the risk of clot fragment dispersal within the patient's vasculature.

An apparatus according to the present invention will comprise catheters adapted for intraluminal introduction into the target body lumen. The dimensions and other physical characteristics of the catheter will vary significantly depending on the body lumen which is to be accessed. In the case of catheters intended for intravascular introduction, the catheter will typically be flexible and may be compatible with introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body. The present invention may also be introduced using a sheath.

Benefits, advantages, and solutions to problems have been described above with regard to particular examples. However, any particular benefit, advantage, or solution is not to be construed as critical, required, or essential. Nor is any particular element that may cause or amplify a benefit, advantage, or solution to be construed as critical, required, or essential.

In the foregoing description, the subject matter has been described with reference to specific exemplary examples. However, it will be appreciated that various modifications and changes may be made without departing from the scope of the present subject matter as set forth herein. The description and figures are to be regarded in an illustrative manner, rather than a restrictive one and all such modifications are intended to be included within the scope of the present subject matter. Accordingly, the scope of the subject matter should be determined by the generic examples described herein and their legal equivalents rather than by merely the specific examples described above.

The examples illustrated have been described to promote clarity of understanding, and it will be obvious that any equivalent modifications will fall within the scope of the appended claims. Equivalent modifications are understood to include, but not be limited by, the following examples: (1) performing the steps recited in a method in any order or skipping steps altogether, (2) varying dimensions and materials within reasonable limits, (3) varying the configuration of elements in way that achieves substantially the same result, and (4) combining different embodiments in a way that achieves substantially the same result.

The present invention, and the embodiments illustrated herein, makes substantial, non-obvious improvements over the prior art. The present invention fragments target substances in a discreet, bite-like manner. The target substance is drawn into the catheter's lumen, and only then does fragmenting occur. The complimentary geometries of the blade and cone enable the device to function like teeth in a mouth. The fragmentation occurs safely within a defined space. The blade and cone come together and impart bi-modal shearing forces (both rotational and axial shearing forces) to fragment a discreet chunk of material. The discreet fragment is then immediately aspirated further within the device's lumen. The cycle of cutting the substance and aspirating a fragment is then repeated. This improves on prior art where the devices fragment target substances within the vasculature, whereby the fragments are simultaneously dispersed throughout the vasculature. Such dispersal can cause further complications that the present invention avoids. The present invention does not release fragments within the vasculature. The creation of the fragments is simultaneous with their removal. Put another way, the present invention improves on prior art by capturing relatively uniform fragments of a targeted substance at a rate equal to the catheter's ability to ingest and clear away the fragmented pieces. The fragments are thereby immediately removed, rather than dispersed into the patient's vasculature.

What is claimed is:

1. A system for removal of one or more target substances from a body passageway, the system comprising:
   a catheter having a lumen, a proximal end, and a distal end, wherein a proximal end of the lumen is configured to be fluidly coupled to an aspiration source;
   a cutting member having a leading cutting edge, the cutting member disposed in the lumen and configured for axial motion within the lumen between a proximal-most position and a distal-most position; and an opposing surface disposed within at a distal location in the lumen, wherein the leading cutting edge of the cutting member is configured to contact the opposing surface and to shear target substance disposed between the leading edge and the opposing surface when the cutting member is positioned in the distal position;

wherein the opposing surface comprises a cone disposed distal to the cutting member, wherein the cutting member is configured so that the leading cutting edge of the cutting member engages a conical surface on the cone as the cutting member is advanced fully in a distal direction.

2. The system of claim 1, wherein the cutting member is further configured for rotation and/or rotational oscillation.

3. The system of claim 2, wherein the system further comprises at least one motor coupled with the cutting member, wherein the at least one motor is configured to impart both rotational motion and reciprocal axial motion to the cutting member.

4. The system of claim 3, wherein the at least one motor is configured to rotate the cutting at a speed of up to 3000 RPM.

5. The system of claim 4, wherein the at least one motor is configured to axially reciprocate the cutting member at a frequency of up to 6 Hz.

6. The system of claim 1, wherein the cutting member is cylindrical with a leading cutting edge.

7. The system of claim 6, wherein the leading cutting edge has cutting teeth.

8. The system of claim 1, wherein a base of the cone is attached to a distal end of the catheter and a pointed conical tip of the cone is directed proximally.

9. The system of claim 8, wherein the cone is configured for rotational motion.

10. The system of claim 1, wherein the catheter includes an atraumatic tip.

11. The system of claim 10, wherein the atraumatic tip comprises a metallic backbone and a polymeric material.

12. The system of claim 11, wherein the metallic backbone comprises a preselected angle or arc.

13. The system of claim 11, wherein the metallic backbone comprises a wound spring.

14. The system of claim 1, wherein the cutting member and the opposing surface are configured to fragment a targeted substance into fragments having discreet and relatively uniform volumes upon axial motion of the cutting member.

15. A system for removal of one or more substances from a body passageway, the system comprising:

a catheter having a lumen, a proximal end, a distal end, and a sidewall, wherein the sidewall comprises an aperture disposed near the distal end of the catheter;

a cone having a base and a tip, the cone positioned at the distal end of the catheter, wherein the base of the cone is oriented toward the distal end of the catheter and the tip of the cone is orientated toward the proximal end of the catheter; and a distally facing cutting member disposed in the lumen of the catheter, the cutting member configured for reciprocal axial translation in both a distal direction toward the cone an a proximal direction away from the cone.

16. The system of claim 15, wherein the system further comprises a motor configured to impart axial motion to the cutting member.

17. The system of claim 15, wherein the cutting member is further configured for rotation and/or rotational oscillation.

18. The system of claim 17, wherein the system further comprises a motor configured to imparts both axial and rotational motion to the cutting member.

19. The system of claim 15, further comprising an aspiration source in fluid communication with the catheter.

20. The system of claim 15, wherein the cutting member is configured to rotate at a speed of up to 3000 RPM.

21. The system of claim 15, wherein the cutting member is configured for axial translation at a frequency of up to 6 Hz.

22. The system of claim 15, wherein the cutting member is cylindrical with a leading cutting edge.

23. The system of claim 22, wherein the leading cutting edge has cutting teeth.

24. The system of claim 15, wherein the cone has a conical surface disposed distal to the cutting member, wherein the cutting member is configured so that the leading cutting edge of the cutting member engages the conical surface on the cone as the cutting member is advanced fully in a distal direction.

25. The system of claim 15, wherein the cone is configured for rotational motion.

26. The system of claim 13, wherein the catheter includes an atraumatic tip.

27. The system of claim 26, wherein the atraumatic tip comprises a metallic backbone and a polymeric material.

28. The system of claim 27, wherein the metallic backbone comprises a preselected angle or arc.

29. The system of claim 27, wherein the metallic backbone comprises a spring.

30. The system of claim 15, wherein the cutting member and the cone are configured to fragment a targeted substance into fragments having discreet and relatively uniform volumes upon axial motion of the cutting member.

* * * * *